United States Patent
Wang et al.

(10) Patent No.: US 12,183,002 B2
(45) Date of Patent: Dec. 31, 2024

(54) HEARING STATE PREDICTION APPARATUS AND METHOD BASED ON DIFFUSION TENSOR IMAGE

(71) Applicant: BEIJING FRIENDSHIP HOSPITAL, CAPITAL MEDICAL UNIVERSITY, Beijing (CN)

(72) Inventors: Zhenchang Wang, Beijing (CN); Xinghao Wang, Beijing (CN); Qian Chen, Beijing (CN); Han Lv, Beijing (CN); Jia Li, Beijing (CN); Jing Sun, Beijing (CN); Linkun Cai, Beijing (CN); Ruowei Tang, Beijing (CN); Pengling Ren, Beijing (CN); Yawen Liu, Beijing (CN); Wenbo Yang, Beijing (CN)

(73) Assignee: BEIJING FRIENDSHIP HOSPITAL, CAPITAL MEDICAL UNIVERSITY, Beijing (CN)

( * ) Notice: Subject to any disclaimer, the term of this patent is extended or adjusted under 35 U.S.C. 154(b) by 0 days.

(21) Appl. No.: 18/634,483

(22) Filed: Apr. 12, 2024

(65) Prior Publication Data
US 2024/0354941 A1    Oct. 24, 2024

(30) Foreign Application Priority Data
Apr. 21, 2023   (CN) .......................... 202310436275.9

(51) Int. Cl.
*G06T 7/00*       (2017.01)
*A61B 5/00*       (2006.01)
(Continued)

(52) U.S. Cl.
CPC .......... *G06T 7/0012* (2013.01); *A61B 5/0042* (2013.01); *A61B 5/055* (2013.01);
(Continued)

(58) Field of Classification Search
CPC . G06T 7/0012; G06T 7/11; G06T 7/50; G06T 2207/10092; G06T 2207/20072;
(Continued)

(56) References Cited

U.S. PATENT DOCUMENTS

| | | | |
|---|---|---|---|
| 6,853,189 | B1 | 2/2005 | Pipe |
| 8,059,879 | B2 | 11/2011 | Tsukimoto |

(Continued)

FOREIGN PATENT DOCUMENTS

| | | | |
|---|---|---|---|
| CN | 101287410 A | 10/2008 | |
| CN | 107330267 A | 11/2017 | |

OTHER PUBLICATIONS

Brown, Colin J., and Ghassan Hamarneh. "Machine learning on human connectome data from MRI." arXiv preprint arXiv:1611.08699 (2016). (Year: 2016).*

(Continued)

*Primary Examiner* — Bobbak Safaipour
(74) *Attorney, Agent, or Firm* — Maschoff Brennan

(57) ABSTRACT

Disclosed are a hearing state prediction apparatus and method based on a diffusion tensor image, including: obtaining a diffusion tensor image to be processed, wherein the diffusion tensor image comprises a diffusion-weighted image; generating a diffusion index image based on the diffusion-weighted image; determining a white matter microstructural feature corresponding to the diffusion tensor image, and determining a hearing state corresponding to the diffusion tensor image according to a mapping relationship between the white matter microstructural feature and the hearing state. The apparatus may generate the diffusion index image through the diffusion-weighted image included in the diffusion tensor image, and then the white matter microstructural feature is determined based on the diffusion index image, so that the white matter microstructural feature (Continued)

can be identified more accurately, and the accuracy of a hearing state evaluation result is improved. Meanwhile, the relation between hearing disorder and brain microstructure change is disclosed.

11 Claims, 4 Drawing Sheets

(51) Int. Cl.
    *A61B 5/055*     (2006.01)
    *A61B 5/12*     (2006.01)
    *G06T 7/11*     (2017.01)
    *G06T 7/50*     (2017.01)
    *G06V 10/44*     (2022.01)

(52) U.S. Cl.
CPC ............ *A61B 5/125* (2013.01); *A61B 5/7267* (2013.01); *A61B 5/7275* (2013.01); *A61B 5/7278* (2013.01); *G06T 7/11* (2017.01); *G06T 7/50* (2017.01); *G06V 10/44* (2022.01); *G06T 2207/10092* (2013.01); *G06T 2207/20072* (2013.01); *G06T 2207/20081* (2013.01); *G06T 2207/30016* (2013.01); *G06V 2201/03* (2022.01)

(58) Field of Classification Search
CPC . G06T 2207/20081; G06T 2207/30016; A61B 5/0042; A61B 5/055; A61B 5/125; A61B 5/7267; A61B 5/7275; A61B 5/7278; G06V 10/44; G06V 2201/03
See application file for complete search history.

(56) References Cited

U.S. PATENT DOCUMENTS

| | | | |
|---|---|---|---|
| 11,393,087 B2* | 7/2022 | Parikh | G16H 20/00 |
| 2021/0082135 A1* | 3/2021 | Xu | G06T 7/529 |
| 2024/0075320 A1* | 3/2024 | Rezai | A61N 1/36082 |
| 2024/0185498 A1* | 6/2024 | Francis | G06T 15/00 |
| 2024/0221162 A1* | 7/2024 | Xie | G06T 7/12 |

OTHER PUBLICATIONS

CN Office Action dated Sep. 1, 2023 as received in Application No. 202310436275.9.

* cited by examiner

HEARING STATE PREDICTION APPARATUS AND METHOD BASED ON DIFFUSION TENSOR IMAGE

FIELD

The present disclosure belongs to the field of computer technology, and in particular, relates to a hearing state prediction apparatus and method based on a diffusion tensor image.

BACKGROUND

In practical applications, noise may cause various hearing disorders, such as decreased auditory sensitivity, increased auditory threshold, auditory dysfunction, and even hearing disorders. There are different clinical management plans for different degrees of hearing disorders. Therefore, the judgment of the degree of hearing disorder is of great significance.

Hearing disorders will not cause visible structural changes in brain white matter, which may only cause abnormal brain white matter microstructural changes, such as alterations in white matter fiber tract density and white matter integrity parameter indices indicators. DTI images can intuitively reflect the microscopic morphology, structural feature, and spatial distribution of brain white matter fiber tracts.

However, DTI images are different from traditional magnetic resonance T1WI or T2WI images, which do not provide fine anatomical structures, making it difficult for professional doctors to make accurate judgments by observing medical imaging with their naked eyes alone. Therefore, a new solution needs to be proposed.

SUMMARY

Given this, the present disclosure provides a hearing state prediction apparatus and method based on diffusion tensor image that solves or partially solves the above technical problems.

In the first aspect, embodiments of the present disclosure provide a hearing state prediction apparatus based on diffusion tensor image. The apparatus includes:
  an obtaining module, configured to obtain a diffusion tensor image to be processed, wherein the diffusion tensor image comprises a diffusion-weighted image;
  a first determining module, configured to generate a diffusion index image according to the diffusion-weighted image; and
  a second determining module, configured to determine a white matter microstructural feature corresponding to the diffusion tensor image according to the diffusion index image, and determine a hearing state corresponding to the white matter microstructural feature according to a mapping relationship between the white matter microstructural feature and the hearing state.

In a second aspect, embodiments of the present disclosure provide a hearing state prediction method based on diffusion tensor image. The method includes:
  obtaining a diffusion tensor image to be processed, wherein the diffusion tensor image comprises a diffusion-weighted image;
  generating a diffusion index image based on the diffusion-weighted image; and
  determining a white matter microstructural feature corresponding to the diffusion tensor image, and determining a hearing state corresponding to the diffusion tensor image according to a mapping relationship between the white matter microstructural feature and the hearing state.

In a third aspect, embodiments of the present disclosure provide an electronic device, including a memory and a processor; where,
  the memory is used to store programs;
  the processor is coupled to the memory and configured to execute the program stored in the memory for:
  obtaining a diffusion tensor image to be processed, where the diffusion tensor image comprises a diffusion-weighted image;
  generating a diffusion index image based on the diffusion-weighted image; and
  determining a white matter microstructural feature corresponding to the diffusion tensor image, and determining a hearing state corresponding to the diffusion tensor image according to a mapping relationship between the white matter microstructural feature and the hearing state.

In a fourth aspect, embodiments of the present disclosure provide a computer storage medium for storing a computer program. The computer program enables the computer to implement the following method when executed:
  obtaining a diffusion tensor image to be processed, where the diffusion tensor image comprises a diffusion-weighted image;
  generating a diffusion index image based on the diffusion-weighted image; and
  determining a white matter microstructural feature corresponding to the diffusion tensor image, and determining a hearing state corresponding to the diffusion tensor image according to a mapping relationship between the white matter microstructural feature and the hearing state.

In the fifth aspect, embodiments of the present disclosure provide a hearing state prediction model training apparatus, the method includes:
  an obtaining module, configured to obtain a diffusion tensor image sample and a preset hearing state corresponding to the diffusion tensor image sample, wherein the diffusion tensor image sample comprises a diffusion-weighted image;
  a first determining module, configured to generate a diffusion index image according to the diffusion-weighted image;
  a second determining module, configured to determine a white matter microstructural feature corresponding to the diffusion tensor image sample according to the diffusion index image, and determine a hearing state corresponding to the diffusion tensor image sample according to a mapping relationship between the white matter microstructural feature and the hearing state; and
  generating module, configured to determine a consistency between the hearing state and the preset hearing state corresponding to the diffusion tensor image sample, when the consistency between the hearing state and the preset hearing state is greater than or equal to a preset threshold, generating a hearing state prediction model.

In a sixth aspect, embodiments of the present disclosure provide a training method for a hearing state prediction model, which includes:
  obtaining a diffusion tensor image sample and a preset hearing state corresponding to the diffusion tensor image sample, wherein the diffusion tensor image sample comprises a diffusion-weighted image;

generating a diffusion index image according to the diffusion-weighted image;

determining a white matter microstructural feature corresponding to the diffusion tensor image sample according to the diffusion index image, and determining a hearing state corresponding to the diffusion tensor image sample according to a mapping relationship between the white matter microstructural feature and the hearing state;

determining a consistency between the hearing state and the preset hearing state corresponding to the diffusion tensor image sample, when the consistency between the hearing state and the preset hearing state is greater than or equal to the preset threshold, a hearing state prediction model is generated.

In a seventh aspect, embodiments of the present disclosure provide an electronic device, including a memory and a processor; where, the memory is used to store programs; the processor is coupled to the memory and configured to execute the program stored in the memory for:

obtaining a diffusion tensor image sample and a preset hearing state corresponding to the diffusion tensor image sample, wherein the diffusion tensor image sample comprises a diffusion-weighted image;

generating a diffusion index image according to the diffusion-weighted image;

determining a white matter microstructural feature corresponding to the diffusion tensor image sample according to the diffusion index image, and determining a hearing state corresponding to the diffusion tensor image sample according to a mapping relationship between the white matter microstructural feature and the hearing state;

determining a consistency between the hearing state and the preset hearing state corresponding to the diffusion tensor image sample, when the consistency between the hearing state and the preset hearing state is greater than or equal to the preset threshold, a hearing state prediction model is generated.

In the eighth aspect, embodiments of the present disclosure provide a computer storage medium for storing a computer program. The computer program enables the computer to implement the following method when executed:

obtaining a diffusion tensor image sample and a preset hearing state corresponding to the diffusion tensor image sample, wherein the diffusion tensor image sample comprises a diffusion-weighted image;

generating a diffusion index image according to the diffusion-weighted image;

determining a white matter microstructural feature corresponding to the diffusion tensor image sample according to the diffusion index image, and determining a hearing state corresponding to the diffusion tensor image sample according to a mapping relationship between the white matter microstructural feature and the hearing state;

determining a consistency between the hearing state and the preset hearing state corresponding to the diffusion tensor image sample, when the consistency between the hearing state and the preset hearing state is greater than or equal to the preset threshold, a hearing state prediction model is generated.

The hearing state prediction scheme provided by the embodiment of the present disclosure obtains the diffusion tensor image to be processed through the obtaining module, where the diffusion tensor image includes a diffusion-weighted image. Then, the first determining module generates a diffusion index image according to the diffusion-weighted image; further, the second determining module determines the white matter microstructural feature corresponding to the diffusion tensor image according to the diffusion index image and determines the hearing state corresponding to the diffusion tensor image according to the mapping relationship between the white matter microstructural feature and the hearing states.

In the technical solution of the present disclosure, the diffusion-weighted image included in the diffusion tensor image can be used to generate a diffusion index image, and then the white matter microstructural feature can be determined based on the diffusion index image, which can more accurately identify the white matter microstructural feature, thereby improving the accuracy of a hearing state evaluation result, meanwhile, the relation between hearing disorder and brain microstructure change is disclosed.

BRIEF DESCRIPTION OF THE DRAWINGS

To describe the technical solutions in the embodiments of the present disclosure or the prior art more clearly, the drawings required to be used for descriptions of the embodiments or the prior art will be simply introduced below. It is apparent that the drawings described below are some embodiments of the present disclosure. Those of ordinary skill in the art may further obtain other drawings according to these drawings without creative work. In the drawings.

DETAILED DESCRIPTION OF EXAMPLE EMBODIMENTS

Figure 1:
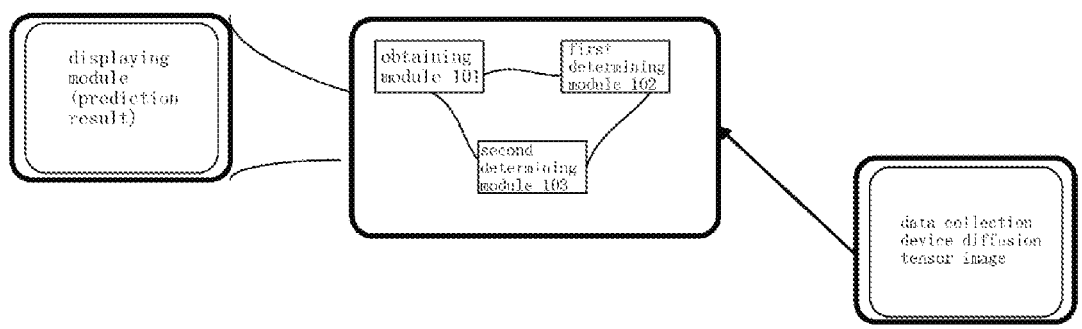
FIG. 1 is a schematic structural diagram of a hearing state prediction apparatus based on a diffusion tensor image according to the embodiments of the present disclosure.

Before introducing the technical solutions provided by each embodiment of the present disclosure, a brief introduction to the terms involved in this article will be given.

To make the purposes, technical solutions, and advantages of the embodiments of the present disclosure clearer, the technical solutions in the embodiments of the present disclosure will be clearly and completely described below in combination with the drawings in the embodiments of the present disclosure. The described embodiments are not all embodiments but part of embodiments of the present disclosure. All other embodiments obtained by those of ordinary skill in the art based on the embodiments in the present disclosure without creative work shall fall within the scope of protection of the present disclosure.

Terms used in the embodiments of the present disclosure are only adopted to describe specific embodiments and are not intended to limit the present disclosure. "A/an", "said" and "the", used in the embodiments and appended claims of the present disclosure, in a singular form are also intended to include a plural form, unless other meanings are clearly represented in the specification. "Multiple" usually includes at least two but does not rule out the inclusion of at least one.

It is to be understood that the term "and/or" used in the present disclosure is only an association relationship describing associated objects and represents the existence of three relationships. For example, A and/or B may represent three conditions, i.e., independent existence of A, coexistence of A and B, and independent existence of B. In addition, the character "/" in the present disclosure usually represents that previous and next associated objects form an "or" relationship.

It should be understood that although the terms first, second, third, etc. may be used to describe XXX in the embodiments of the present disclosure, these XXX should not be limited only to those terms. These terms are only used to distinguish XXX from each other. For example, a first XXX may also be referred to as a second XXX without departing from the scope of the embodiments of the present disclosure. Similarly, a second XXX may also be referred to as a first XXX. Depending on the context, the words "if" and "in case of" used herein may be interpreted to mean "when" or "while" or "in response to determining" or "in response to monitoring". Similarly, depending on the context, the phrase "if determined" or "if monitored (conditions or events stated)" can be interpreted as "when determined" or "in response to determination" or "when monitored (stated condition or event)" or "in response to monitor (conditions or events stated)".

It should also be noted that the terms "including", "containing" or any other variations thereof are intended to encompass a non-exclusive inclusion, such that the item or system including a series of elements includes not only those elements but also other elements not explicitly listed, or elements that are inherent to such item or system. In the absence of more restrictions, an element defined by the phrase "including one . . . " does not exclude the existence of additional identical elements in the item or system that includes the element.

First, it is necessary to introduce the implementation background of the present disclosure. Currently, magnetic resonance diffusion tensor imaging (DTI) is the only non-invasive examination method that can effectively observe and track brain white matter fiber tracts in vivo. It measures and records the diffusion trajectory of water molecules in biological tissues, tracks the diffusion movement of water molecules in brain structures, and constructs a three-dimensional space diffusion characteristic image. DTI can visually display the micromorphological structural feature and spatial distribution of fiber tracts, which is mainly used for observation and tracking of the brain, especially white matter tracts, research on brain development and brain cognitive functions, pathological changes in brain diseases, and pre-planning and post-operative evaluation for brain surgery.

Hearing disorders, also known as deafness, are the number of decibels by which the human ear's hearing threshold at a certain frequency is higher than the normal hearing threshold. Decreased hearing sensitivity, increased hearing threshold, auditory dysfunction, and even hearing disorders caused by noise are collectively called hearing disorders, which can be divided into two types: temporary and permanent. At the same time, the International Health Organization classifies hearing disorders as follows: the average hearing disorder is less than or equal to 25 decibels, which is normal; the average hearing disorder is between 26 and 40 decibels, which is mild hearing disorders; the average hearing disorder is between 41 and 60 decibels, which is moderate hearing disorder; the average hearing disorder between 61 and 80 decibels, which is severe hearing disorder; an average hearing disorder greater than or equal to 81 decibels, which is extremely severe hearing disorder. There are different clinical management plans for different degrees of hearing disorder, so the judgment of the degree of hearing disorder is of great significance.

DTI technology can intuitively reflect the microscopic morphology, structural feature, and spatial distribution of white matter fiber tracts in the brain, and can be used to accurately infer pathophysiological changes. Regardless of the severity, hearing disorder does not cause visible structural changes in the white matter of the brain, such as changes in whole-brain morphology, including whole-brain atrophy, reduced white matter volume, white matter hyperintensity, etc., but it can cause abnormal changes in the microstructure of the white matter, such as abnormal changes in white matter fiber tract density and white matter integrity parameter indicators.

However, DTI images are different from traditional magnetic resonance T1WI or T2WI images, which do not have fine anatomical structures. It is difficult for professional doctors to make judgments through medical imaging observation only with their bare eyes. They usually extract the pixel values of the relevant images for statistical analysis or judgment. This only takes into account the differences in the overall image, and cannot conduct more detailed and in-depth research on features such as white matter microstructure, making it impossible to accurately determine the hearing state of the assessment target directly based on DTI images.

Therefore, a technical solution that can solve at least one of the above problems remains to be proposed.

The execution subject of the technical solutions provided by the embodiments of the present disclosure may be one apparatus or multiple apparatuses. The apparatus may include but is not limited to an apparatus integrated on any terminal device such as a smartphone, tablet computer, PDA (Personal Digital Assistant), smart TV, laptop computer, desktop computer, smart wearable device, etc. Said apparatus includes an obtaining module for obtaining data to be processed (such as a diffusion tensor image introduced below), and a first determining module and a second determining module for analyzing and processing the data to be processed. The first determining module and the second determining module of the apparatus may be installed in the above-mentioned terminal device. The first determining module and the second determining module of the apparatus may be integrated in the same device as the obtaining module, or may be integrated in different devices respectively, which is not limited by the embodiments of the present disclosure. Optionally, the apparatus further includes a display module for displaying processing results of the apparatus, such as a screen in a terminal device.

In practical applications, the obtaining module of the apparatus can be connected to an inspection apparatus integrated with magnetic resonance, and the inspection apparatus is disposed on the side of the target evaluation object. The inspection apparatus is implemented as, for example, a brain inspection apparatus integrated with magnetic resonance, which is connected to an apparatus integrated with the obtaining module. Of course, in order to adapt to various application scenarios, the connection method between the brain inspection apparatus and the apparatus integrating the first determining module and the second determining module can be a wired connection or a wireless connection, such as Wi-Fi, 5G, 4G, Bluetooth, etc.

In another embodiment, the obtaining module, the first determining module, and the second determining module can be integrated in the same device. For example, the obtaining module, the first determining module, and the second determining module can be integrated in a data analysis apparatus connected to the brain inspection apparatus. Furthermore, after obtaining the data to be processed from the brain examination apparatus, the data analysis apparatus analyzes the data to be processed and displays the processing results, such as issuing voice information for early warning or displaying the hearing state. Alternatively, the brain inspection apparatus sends the data to be processed to a terminal device with a function of analyzing the data to be processed, and the terminal device displays the processing results.

In fact, the hardware structure of the apparatus can be set according to specific application scenarios. The embodiments of the present disclosure are only examples rather than limiting.

It should be noted that no matter which hardware structure the execution subject is implemented as, the core intention of the execution subject is: obtaining the diffusion tensor image to be processed, where the diffusion tensor image includes a diffusion weighted image; generating a diffusion index image according to the diffusion weighted image; then determining the white matter microstructural feature corresponding to the diffusion tensor image according to the diffusion index image, and determining the hearing state corresponding to the diffusion tensor image according to a mapping relationship between the white matter microstructural feature and the hearing state, which greatly simplifies the obtaining of hearing state, expands the application scenarios of hearing tests, improves the accuracy of hearing state and hearing function assessment results, and reveals the connection between hearing disorder and changes in brain microstructure.

The specific implementation of the technical solution will be introduced below with reference to specific embodiments.

FIG. 1 is a schematic structural diagram of a hearing state prediction apparatus based on a diffusion tensor image according to the embodiments of the present disclosure. As shown in FIG. 1, the apparatus includes the following modules:
  an obtaining module 101, configured to obtain a diffusion tensor image to be processed, where the diffusion tensor image includes a diffusion weighted image;
  a first determining module 102, configured to generate a diffusion index image according to the diffusion weighted image; and
  a second determining module 103, configured to determine the white matter microstructural feature corresponding to the diffusion tensor image according to the diffusion index image, and determine the hearing state corresponding to the diffusion tensor image according to the mapping relationship between the white matter microstructural feature and hearing state.

Further, the apparatus may further include a display module for outputting the processing result of the second determining module 103, such as the hearing state corresponding to the diffusion tensor image.

It can be understood that the obtaining module 101, the first determining module 102, and the second determining module 103 can be located on the same device, or the obtaining module 101 can be located locally, and the first determining module 102 and the second determining module 103 located on the remote server. Of course, the two structures described here are only examples. In actual applications, the hardware structure for integrating the obtaining module 101 with the first determining module 102 and the second determining module 103 can be selected according to specific application scenarios.

In the present embodiment, the apparatus can analyze and process the brain diffusion tensor image of the evaluation target to obtain the hearing state corresponding to the diffusion tensor image. Specifically, the hearing state can be divided into several categories according to the degree of hearing disorder: normal hearing, mild hearing disorder, moderate hearing disorder, severe hearing disorder, extremely severe hearing disorder, etc. Each hearing state can also be set according to actual needs.

When the apparatus analyzes and processes the diffusion tensor image, first, the obtaining module 101 can obtain the diffusion tensor image to be processed. Specifically, the diffusion tensor image to be processed may be a diffusion tensor image of the brain, and the diffusion tensor image includes a diffusion weighted image. In an optional embodiment, the obtaining module 101 can communicate with the data collection device, thereby receiving physiological feature data from the data collection device through the communication connection with the data collection device. For example, the diffusion tensor image to be processed can be obtained directly by receiving the diffusion tensor image from a magnetic resonance scanner. Since the diffusion tensor image of the brain can intuitively reflect the microscopic morphology, the structural feature and spatial distribution of the brain white matter fiber tracts, the collected diffusion tensor image can reflect the microstructure of the brain white matter to a certain extent, thereby facilitating subsequently, a mapping relationship between the brain white matter microstructure and the hearing state will be established to provide a basis for predicting hearing state.

In practical applications, the generally collected diffusion tensor images are DICOM images. The original collected DTI images are preprocessed and the original DICOM images are converted into NIFTI format to directly obtain the Diffusion weighted image, the diffusion gradient table and the diffusion b-value table corresponding to the diffusion image to be processed.

Then, the first determining module 102 generates a diffusion index image according to the diffusion weighted image. The first determining module 102 mentioned in the embodiment of the present disclosure is used to identify and process the collected diffusion weighted image. After obtaining the diffusion weighted image, the first determining module 102 uses the diffusion weighted image to determine the diffusion index image corresponding to the diffusion weighted image. Specifically, the diffusion index image refers to a parameter image that reflects the white matter microstructure. For example, the diffusion index image includes one or a combination of the following: fractional anisotropy map (FA map), mean diffusion coefficient map (MD map), and axial diffusion map (AD map), and radial diffusion map (RD map), etc.

In an optional embodiment, when the first determining module generates the diffusion index image according to the diffusion weighted image, it is specifically configured to: determine the diffusion tensor according to the diffusion weighted image; determine the diffusion eigenvalue according to the diffusion tensor; determine the diffusion index data according to the diffusion eigenvalue; generate diffusion index image according to the diffusion index data. Specifically, the diffusion index data are white matter microstructural parameters, which are commonly used index data when analyzing and processing diffusion tensor image. The diffusion index data can include: apparent diffusion coefficient (ADC), fractional anisotropy (FA), mean diffusivity (MD), relative anisotropy (RA), axial diffusivity (AD), radial diffusivity (RD).

ADC measures the diffusion movement of water molecules in the human tissue environment, that is, all factors (random and non-random) that affect the movement of water molecules are superimposed into an observation value, reflecting the displacement intensity of water molecules in the direction of the diffusion sensitive gradient. FA measures the integrity of white matter, which refers to the proportion of anisotropic components of water molecules in the entire diffusion tensor, ranging from 0 to 1. Specifically, 0 represents unrestricted diffusion. For example, the FA value of cerebrospinal fluid is close to 0. For very regular and directional tissues, the FA value is greater than 0. For example, the FA value of brain white matter fibers is close to 1. MD reflects the overall diffusion level and diffusion resistance of molecules. MD only represents the size of diffusion and has nothing to do with the direction of diffusion. AD is a symptom of axonal damage, which is negatively correlated with axonal damage and positively correlated with axonal repair. RD reflects myelination of nerve fibers but is also affected by axonal damage or a reduction in axonal density in a specific area. Therefore, white matter microstructural feature can be determined from these diffusion index data. Specifically, the white matter microstructural feature can reflect the white matter loss degree feature.

Specifically, a single exponential diffusion model is used to linearly fit the diffusion tensor according to the principle of least squares, to extract the diffusion eigenvalue, and then the diffusion index data FA value, MD value, AD value and RD value are calculated according to the diffusion eigenvalue, and generate FA map according to the FA value, MD map according to the MD value, AD map according to the AD value, and RD map according to the RD value. These diffusion index images can better characterize the microstructural feature of white matter from all aspects, and more accurately and comprehensively reflect the microstructural feature of white matter corresponding to the diffusion tensor image to be processed.

After determining the white matter microstructural feature corresponding to the diffusion tensor image, the second determining module determines the white matter microstructural feature corresponding to the diffusion tensor image according to the diffusion index image, and determines the hearing state corresponding to the diffusion tensor image according to the relationship between the white matter microstructural feature and the hearing state.

For example, the higher the ADC value, the stronger the diffusion movement of water molecules in the tissue. When the white matter is damaged, the ADC value decreases. FA represents the myelination of white matter fiber. When white matter is damaged and demyelinated, the FA value decreases. The larger the MD, the freer water molecules are contained in the tissue. MD mainly reflects myelination, but is also related to the density of nerve cell membranes and is sensitive to cell necrosis and edema. MD increases when white matter is damaged. And when white matter is damaged, AD decreases and RD increases. Then, the loss condition of the white matter microstructure can be determined according to the image feature and the numerical value feature in the diffusion index map. Based on the relationship between the loss condition of the white matter microstructure and the hearing disorder, the hearing disorder condition is further determined, and the corresponding hearing state is obtained correspondingly.

Optionally, the second determining module in the apparatus can also be configured to: set the white matter microstructural feature threshold corresponding to each hearing state category. Then, after the white matter microstructural feature is determined, the hearing state to which the white matter microstructure belongs can be determined according to the white matter microstructural feature and the white matter microstructural feature threshold corresponding to each hearing state. For example, if the white matter microstructural feature threshold is 20% white matter damage, the corresponding hearing state is mild hearing disorder.

In order to make the entire prediction process simpler, the present disclosure can directly determine the hearing state based on the depth feature information in the diffusion index image, directly establish the mapping relationship between the depth feature information and the hearing state, and based on the mapping relationship between the depth feature information and the hearing state, determine the hearing state corresponding to the depth feature information. Further optionally, when the second determining module 103 determines the white matter microstructural feature corresponding to the diffusion tensor image according to the diffusion index image, and determines the white matter microstructural feature corresponding to the diffusion tensor image according to the mapping relationship between the white matter microstructural feature and the hearing state, it is specifically configured to: perform feature extraction on the diffusion index image to obtain a first depth feature; perform segmentation on the diffusion index image to obtain multiple segmented regions; perform feature extraction on the multiple segmented regions to obtain a second depth feature; and input the first depth feature and the second depth feature to a first deep learning model to obtain a hearing state corresponding to the depth feature, and the first deep learning model is trained to determine the hearing state. Various deep features of the diffusion index image are further explored, and the pre-trained first deep learning model is used to analyze the features of the diffusion index image from multiple angles to determine the hearing state, which improves the accuracy of the hearing state prediction results.

The first deep learning model may be trained based on the first depth feature sample, the second depth feature sample in the diffusion index image, and the hearing state sample of the diffusion index image. Optionally, the deep learning model may include but is not limited to: a Seq2Seq model including an encoder (Encoder) and a decoder (Decoder). The Seq2Seq model is a deep learning model based on Long Short-Term Memory (LSTM). For example, the Seq2Seq model includes: an encoder and a decoder built based on LSTM.

For example, in the above steps, it is assumed that the first depth feature data and the second depth feature data are sequence data. Assume that the pre-trained first deep learning model is the Seq2Seq model. Based on the above assumption, the first depth feature sequence is converted into a first depth feature vector through the encoder, and the second depth feature sequence is converted into a second depth feature vector. Specifically, the length of the depth feature vector can be fixed. Furthermore, the first depth feature vector and the second depth feature vector are input into the decoder of the Seq2Seq model to obtain the sequence corresponding to the depth feature vector (i.e., the predicted hearing state).

Figure 2:
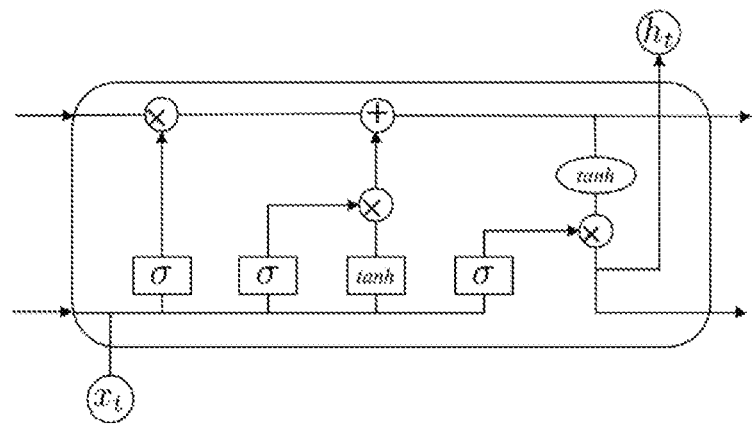
FIG. 2 is a schematic diagram of the principle of a hearing state prediction apparatus based on a diffusion tensor image according to the embodiments of the present disclosure.

In addition, the first deep learning model can also be implemented as: a model based on a Gate Recurrent Unit (GRU), or a deep learning model built based on Transformer. In the deep learning model built based on LSTM, specifically, by adding intermediate cell state information for back propagation, a better prediction effect can be obtained. In an optional embodiment, as shown in FIG. 2, three control switches are added inside the deep learning model (such as the Seq2Seq model): a forget gate (Forget Gate), an input gate (Input Gate), and an output gate (Output Gate).

Specifically, in the deep learning model, the forgetting gate $f_t$ is obtained from the current input $x_t$ and a previous output $h_{t-1}$, and $f_t$ determines what content to discard from the previous cell state $C_{t-1}$. Each value in $f_t$ is a number from 0 to 1, with 1 representing complete retention and 0 representing complete deletion. The specific implementation of the forget gate $f_t$ is as follows:

$$f_t = \sigma(w_f \cdot h_{t-1} + u_f \cdot x_t + b_f) \quad \text{formulation 2}$$

The input gate $i_t$ is used to update important information. For example, $i_t$ is obtained from the current input $x_t$ and a previous output $h_{t-1}$, and $i_t$ is used to determine the new information that needs to be entered into the current cell state $C_t$. The new information is represented here by $\tilde{C}_t$. The specific implementation of input gate $i_t$ is as follows:

$$i_t = \sigma(w_i \cdot h_{t-1} + u_i \cdot x_t + b_i) \quad \text{formulation 3}$$

$$\tilde{c}_t = \tanh(w_c \cdot h_{t-1} + u_c \cdot x_t + b_c) \quad \text{formulation 4}$$

$$c_t = f_t \odot C_t + i_t \odot \tilde{c}_t \quad \text{formulation 5}$$

The output gate $o_t$ is used to determine the output value of the model. $o_t$ determines how much information is output to $h_t$. The specific implementation of the output gate $o_t$ is as follows:

$$o_t = \sigma(w_o \cdot h_{t-1} + u_o \cdot x_t + b_o) \quad \text{formulation 6}$$

$$h_t = o_t \tanh \odot (C_t) \quad \text{formulation 7}$$

Of course, in addition to the Seq2Seq model introduced above, other deep learning models or other neural networks can also be used to implement the prediction function of the second determining module 103 introduced above, which is not limited in the present disclosure.

In order to improve the accuracy of the model and avoid model overfitting. Before using the Seq2Seq model to analyze and process the first depth feature and the second depth feature, dimensionality reduction processing may also be included. Specifically, dimensionality reduction is performed on the extracted first depth feature and second depth feature, and the first depth feature and second depth feature after dimensionality reduction are obtained to eliminate strong collinearity in the data and avoid overfitting phenomenon of the model, thus affecting the accuracy of the model. For example, high correlation filtering, LASSO, reverse feature elimination, principal component analysis, local linear embedding and other methods can be used to reduce the dimensionality of the first depth feature and the second depth feature.

In this embodiment, the first determining module generates a diffusion index image by using the diffusion weighted image included in the diffusion tensor image, and then the second determining module determines the white matter microstructural feature based on the diffusion index image, which can more accurately identify the white matter microstructure feature, thereby improving the accuracy of hearing state assessment results, while revealing the connection between hearing disorder and brain microstructural changes.

In addition to the above embodiments, in an optional embodiment, the cerebral perfusion state classification apparatus provided in FIG. 1 also has other implementations. It can be seen from FIG. 1 that the apparatus includes the following modules: an obtaining module 101, a first determining module 102, and a second determining module 103.

In practical applications, when an MRI scanner scans the head of an evaluation target, the eddy currents of the gradient coil can easily cause deformation of the obtained diffusion tensor image, and due to the long DTI acquisition time, head movement between different scan volumes can cause of poor alignment. Then, after the obtaining module 101 obtains the diffusion weighted image, the first determining module 102 can perform eddy current correction processing on the diffusion weighted image.

The brain structures included in the diffusion weighted image include not only brain white matter structures but also other tissues. In order to reduce the calculation time of the DTI fitting and tracking process and improve the accuracy of spatial registration, the first determining module 102 can also perform detissue process on the diffusion weighted image after the eddy current correction processing, to remove all tissues except brain tissue to obtain a diffusion weighted image after brain peeling.

Then, after the first determining module 102 obtains the diffusion weighted image after brain peeling by processing the diffusion weighted image, the second determining module 103 can use the same processing method as described above to process the diffusion weighted image after brain peeling to generate diffusion index image. For the detailed processing process, reference can be made to the processing process of the diffusion weighted image by the second determining module 103 in the above embodiment, which will not be described again here.

In practical applications, the obtained diffusion index image may have problems such as image noise, which affects the results of image analysis and processing. Therefore, it is necessary to eliminate image noise, improve image quality, enrich information, enhance image interpretation and recognition effects, and meet specific analysis requirements. According to the needs, the obtained diffusion index image is enhanced. Optionally, when the second determining module 103 determines the white matter microstructural feature corresponding to the diffusion tensor image according to the diffusion index image, it is specifically configured to: perform filtering processing on the diffusion index image to obtain the processed diffusion index image; perform feature extraction on the processed diffusion index image to obtain a third depth feature; perform segmentation on the processed diffusion index image to obtain multiple segmented regions; perform feature extraction on the multiple segmented regions to obtain a fourth depth feature; and determine the white matter microstructural features corresponding to the diffusion tensor image according to the third depth feature and the fourth depth feature.

For example, the third depth feature is extracted from the brain structure included in the processed diffusion index image, and the brain structure included in the processed diffusion tensor image is segmented based on the AAL template (Anatomical Automatic Labeling) to obtain multiple brain regions. The fourth depth feature is extracted in each brain area, and the white matter microstructural feature corresponding to the diffusion tensor image is determined according to the third depth feature and the fourth depth feature. In this embodiment, not only the overall depth feature of the diffusion tensor image is extracted, but also the local depth feature corresponding to each segmented area is extracted. The white matter microstructural feature corresponding to the secret tensor image is determined from the overall image features and local image feature information respectively, which can more accurately identify white matter microstructural feature, thereby further improving the prediction result of hearing state.

In addition, in order to improve the accuracy of the identified white matter microstructural feature, a machine learning model can be used to extract the third depth feature and the fourth depth feature in the processed diffusion index image. In an optional embodiment, the second determining module performing feature extraction on the processed diffusion index image to obtain the third depth feature, is specifically configured to: use the first machine learning model to analyze and process the processed diffusion index image, obtain a depth feature generation graph corresponding to the processed diffusion index image, and the first machine learning model is trained to determine the depth feature generation graph; perform downsampling on the depth feature generation graph to obtain a depth feature graph; extract a gray level co-occurrence matrix based on the depth feature graph; and the gray level co-occurrence matrix is determined as the third depth feature.

Specifically, the first machine learning model can be trained based on the processed diffusion index image sample and the depth feature generation graph corresponding to the diffusion index image sample. Optionally, the first machine learning model includes but is not limited to: an adversarial diffusion model containing mixed noise, a convolutional neural network model, etc.

For example, the construction process of the adversarial diffusion model of mixed noise may include: selecting mixed noise. Then based on the selected mixed noise, mixed noise is continuously added to the original image (processed diffusion index image sample) according to the time sequence T, until the original image at time t completely becomes a generated image formed by the superposition of two mixed noises; and the images form t–1 to which noise is initially applied are used as the training group, and the original image is input as labels into the generative adversarial network for model training. Then, based on the Euclidean geometric distance between the generated image and the original image plus the difference between the mixed noise parameter corresponding to the generated image and the real applied noise parameter, jointly used as the loss function of the model, the model is trained until the loss function tends to converge. Finally, the model trained in the above steps is saved to obtain the trained adversarial diffusion model based on mixed noise.

Specifically, when selecting mixed noise, the noise selection range includes but is not limited to salt and pepper noise, Gaussian noise, Poisson noise, and multiplicative noise. Any two of these noises are selected and applied to the original image at the same time to form mixed noise.

After using the first machine learning model to obtain the depth feature generation graph corresponding to the processed diffusion index image, the second determining module 103 can also be used to: perform sampling on the kernel by applying a 3×3 convolution to the depth feature generation graph, and then the Markov chain Monte Carlo sampling method is used to resample the convolved image to obtain the downsampled depth feature map. Downsampling the depth feature generation graph can further reduce the image size and highlight the important features of the overall image.

In this embodiment, the adversarial diffusion model theory based on mixed noise is combined with the downsampling method to extract the depth feature information of the processed diffusion index image, which can effectively improve the performance of the obtained image depth feature information, thereby improving the accuracy of hearing state prediction result.

After extracting the third depth feature, the second determining module 103 performs feature extraction on multiple segmented regions, and when obtaining the fourth depth feature, is specifically used to: use the second machine learning model to analyze and process the multiple segmented regions, and obtain fourth depth feature information corresponding to multiple segmented regions, the second machine learning model is trained to obtain depth feature corresponding to the segmented regions.

The second machine learning model may be trained based on multiple segmented region samples corresponding to the processed diffusion index image and depth feature corresponding to the diffusion index image sample. Optionally, the second machine learning model includes but is not limited to: convolutional neural network model, etc.

In an optional embodiment, the specific implementation method of performing segmentation on the processed diffusion index image to obtain multiple segmented regions; performing feature extraction on the multiple segmented regions to obtain the fourth depth feature, may include: the second determining module 103 using the first machine learning model to analyze and process multiple segmented regions to obtain a depth feature generation graph corresponding to the multiple segmented regions. The first machine learning model is trained to determine the depth feature generation graph; performing downsample on each depth feature generation graph to obtain respective corresponding depth feature graphs; based on each depth feature graphs, extracting respective corresponding gray level co-occurrence matrices; and determining multiple gray level co-occurrence matrices as the fourth depth feature.

After the third depth feature and the fourth depth feature are extracted, the white matter microstructural feature corresponding to the diffusion tensor image is determined according to the third depth feature and the fourth depth feature. The mapping relationship between the third depth feature, the fourth depth feature and the white matter microstructural feature can be established in advance to use the mapping relationship to determine the white matter microstructural feature corresponding to the depth feature.

Based on the third machine learning model, the mapping relationship between the third depth feature, the fourth depth feature and the white matter microstructural feature is established, which can more accurately identify the white matter microstructural feature, thus improving the accuracy of the hearing state assessment result. At the same time, the connection between the hearing disorder and brain microstructural changes is revealed. Optionally, the second determining module 103 determining the white matter microstructural feature corresponding to the diffusion tensor image according to the third depth feature and the fourth depth feature, is specifically configured to: input the third depth feature and the fourth depth feature into the fourth machine learning model to obtain the white matter microstructural feature corresponding to the depth feature, and the third machine learning model is trained to obtain the white matter microstructural feature corresponding to the depth feature.

After the white matter microstructural feature is determined, the hearing state category to which the white matter microstructure belongs is determined according to the white matter microstructural feature and the white matter microstructural feature threshold corresponding to the hearing state category. In this way, the hearing state assessment result obtained through analysis and processing is more accurate.

Usually, when predicting hearing state, it is usually necessary to rely on the experience and observation of relevant technical personnel, making it difficult to guarantee the accuracy of the prediction result. In order to solve this technical problem, this embodiment provides a new hearing state prediction method.

Figure 3:
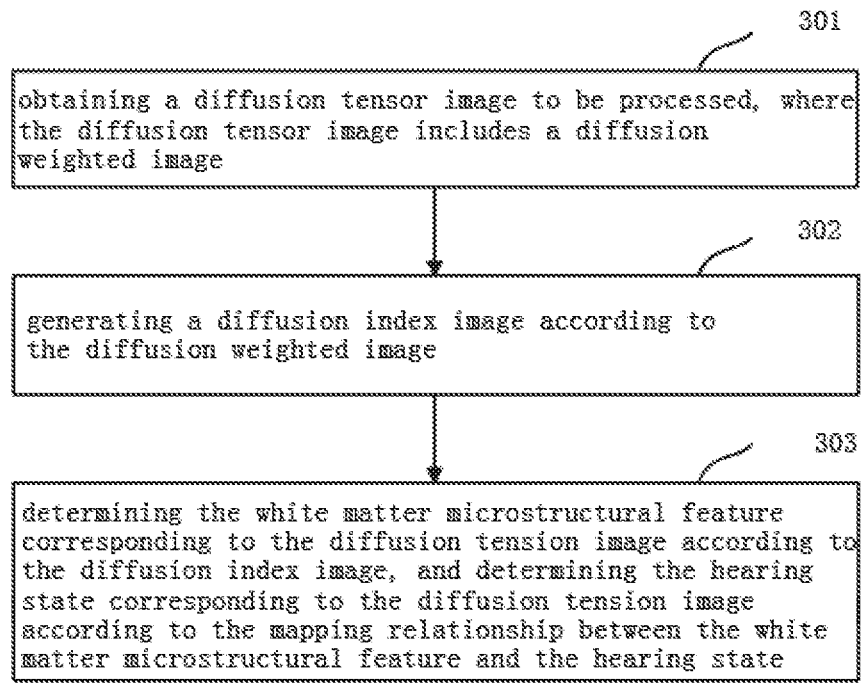
FIG. 3 is a schematic flow chart of a hearing state prediction method based on a diffusion tensor image according to the embodiments of the present disclosure.

FIG. 3 is a schematic flowchart of a hearing state prediction method based on a diffusion tensor image according to the embodiments of the present disclosure. Specifically, it includes the following steps:

301. obtaining a diffusion tensor image to be processed, where the diffusion tensor image includes a diffusion weighted image;

302. generating a diffusion index image according to the diffusion weighted image; and 303. determining the white matter microstructural feature corresponding to the diffusion tensor image according to the diffusion index image, and determining the hearing state corresponding to the diffusion tensor image according to the mapping relationship between the white matter microstructural feature and the hearing state.

In the hearing state prediction solution provided in this embodiment, the diffusion tensor image to be processed can be analyzed and processed to obtain the hearing state corresponding to the diffusion tensor image. According to the degree of hearing disorder, the hearing state is divided into normal hearing, mild hearing disorder, moderate hearing disorder, severe hearing disorder, extremely severe hearing disorder, etc. Each hearing state can also be set according to actual needs.

When performing hearing state prediction, the diffusion tensor image of the evaluation target is first obtained. The diffusion tensor image is a diffusion tensor image obtained after scanning the brain of the evaluation target, and the diffusion tensor image includes a diffusion weighted image.

In order to eliminate the interference of different sampling machines or different imaging parameters, after obtaining the original diffusion tensor image of the evaluation target, the original diffusion tensor image is preprocessed. The original diffusion tensor image is generally a DICOM image. By converting the original DICOM image into NIFTI format, the diffusion weighted image, diffusion gradient table and diffusion b value table of the evaluation target can be directly obtained.

Then, in order to remove the image deformation caused by the eddy current of the gradient coil, as well as the long DTI acquisition time and poor alignment caused by head movement between different scan volumes, the diffusion weighted image was subjected to eddy current correction processing to obtain the corrected diffusion weighted image.

Furthermore, in order to reduce the calculation time of the DTI fitting and tracking process and improve the accuracy of spatial registration, tissue removal processing can also be performed on the corrected diffusion weighted image to remove all tissues except brain tissue to obtain the diffusion weighted image after tissue removal.

Next, the diffusion weighted image is processed to generate a diffusion index image. For example, the diffusion index image can reflect the brain white matter microstructural feature from many aspects. This diffusion index image can lay the foundation for the next step to determine the hearing state corresponding to the microstructural features of the brain white matter. Optionally, the diffusion index image includes one or a combination of the following: fractional anisotropy map, average diffusion coefficient map, axial diffusion coefficient map, radial diffusion coefficient map.

In an optional embodiment, the specific implementation method of generating the diffusion index image according to the diffusion weighted image may be: determining the diffusion tensor according to the diffusion weighted image; determining the diffusion eigenvalue according to the diffusion tensor; determining the diffusion index data according to the diffusion eigenvalue; and generating a diffusion index image according to the diffusion index data.

In practical applications, the obtained diffusion index image may have problems such as image noise, which affects the results of image analysis and processing. Therefore, it is necessary to eliminate image noise, improve image quality, enrich information, enhance image interpretation and recognition effects, and meet specific analysis requirements. According to the needs, the obtained diffusion index image is enhanced. Specifically, the diffusion index image is filtered to obtain a processed diffusion index image.

Next, according to the processed diffusion index image, the white matter microstructural feature corresponding to the diffusion tensor image is determined, and according to the mapping relationship between the white matter microstructural feature and the hearing state, the hearing state corresponding to the diffusion tensor image is determined. Optionally, this method can also set the white matter microstructural feature threshold corresponding to each hearing state in advance. After determining the white matter microstructural feature, the hearing state to which white matter microstructure belongs is determined according to the white matter microstructural feature and the white matter microstructural feature threshold corresponding to each hearing state.

In order to make the entire prediction process simpler, the hearing state can be determined directly based on the depth feature information in the diffusion index image, the mapping relationship between the depth feature information and the hearing state can be directly established, and based on the mapping relationship between the depth feature information and the hearing state, the hearing state corresponding to the depth feature information is determined. Specifically, feature extraction is performed on the diffusion index image to obtain the first depth feature; segmentation of the diffusion index image is performed to obtain multiple segmented regions; feature extraction is performed on the multiple segmented regions to obtain the second depth feature; the first depth feature and the second deep feature are input to the first deep learning model to obtain a hearing state corresponding to the deep feature, where the first deep learning model is trained to determine the hearing state.

Optionally, the first deep learning model may include but is not limited to: a Seq2Seq model including an encoder (Encoder) and a decoder (Decoder). The Seq2Seq model is a deep learning model based on Long Short-Term Memory (LSTM). For example, the Seq2Seq model includes: an encoder and a decoder built based on LSTM.

For example, the convolutional neural network can be used to perform deep feature extract from the diffusion index image to obtain the first depth feature, and the convolutional neural network can be used to perform feature extract from multiple segmented regions to obtain the second depth feature. The first depth feature and the second depth feature can be obtained more accurately, thereby further accurately identifying white matter microstructural feature.

It is worth noting that the hearing state prediction method is similar to the implementation of the hearing state prediction apparatus provided in FIG. 1. The similarities are as mentioned above and will not be elaborated here.

To sum up, in this embodiment, the diffusion index image is generated by using the diffusion weighted image included in the diffusion tensor image, and then the white matter microstructural feature is determined based on the diffusion index image, so that the white matter microstructural feature can be more accurately identified, thereby improving the accuracy of hearing state assessment results and assisting doctors in completing hearing function tests.

In order to improve the accuracy and stability of the prediction results, the diffusion index image after filtering is further analyzed and processed, and feature extraction is performed on the processed diffusion index image to obtain the third depth feature; the processed diffusion index image is segmented to obtain multiple segmented regions; feature is extracted from the multiple segmented regions to obtain fourth depth feature; and the white matter microstructural feature corresponding to the diffusion tensor image is determined according to the third depth feature and the fourth depth feature.

In an optional embodiment, a first machine learning model can be used to analyze and process the processed diffusion index image to obtain a depth feature generation graph corresponding to the processed diffusion index image, and the first machine learning model is trained to determine the depth feature generation graph; the depth feature generation graph is downsampled to obtain the depth feature graph; the gray level co-occurrence matrix is extracted based on the depth feature graph; and the gray level co-occurrence matrix is determined as the third depth feature.

Optionally, the first machine learning model includes: an adversarial diffusion model containing mixed noise. Combining the adversarial diffusion model theory based on mixed noise with the downsampling method to determine the third depth feature corresponding to the processed diffusion index image can further improve the accuracy of the extracted depth feature information.

After obtaining the third depth feature, in order to improve the stability and accuracy of the method, optionally, a second machine learning model is used to analyze and process the multiple segmented regions to obtain the fourth depth feature corresponding to each of the multiple segmented regions. The second machine learning model is trained to obtain depth feature corresponding to the segmented regions.

Then, based on the third depth feature and the fourth depth feature, the white matter microstructural feature corresponding to the diffusion tensor image is determined.

Specifically, a preset relationship between the third depth feature and the fourth depth feature and the white matter microstructural feature is established. After the third depth feature and the fourth depth feature are determined, the white matter microstructural feature is determined based on the preset relationship.

In an optional embodiment, a third machine learning model may be used to establish a preset relationship between the third depth feature and the fourth depth feature and the white matter microstructural feature, so as to determine the white matter microstructural feature using the third machine learning model.

Finally, after the white matter microstructural feature is determined, the hearing state category to which the white matter microstructure belongs is determined based on the white matter microstructural feature and the white matter microstructural feature threshold corresponding to each hearing state.

Figure 4:
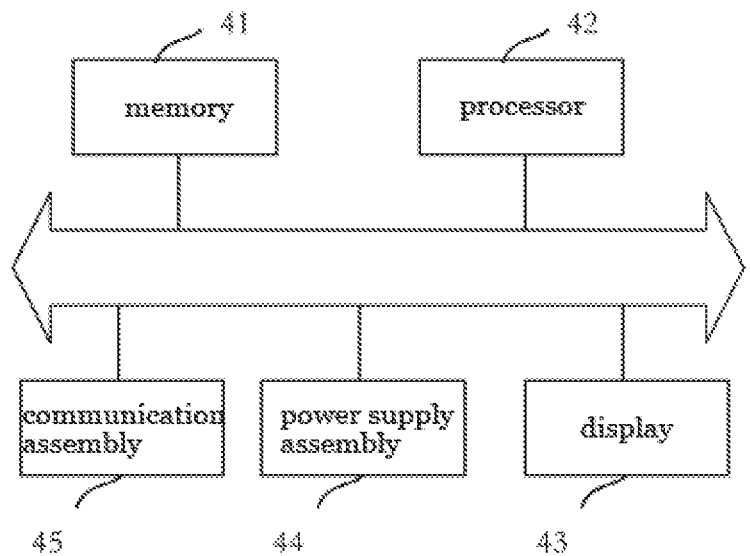
FIG. 4 is a schematic structural diagram of an electronic device according to the embodiments of the present disclosure.

FIG. 4 is a schematic structural diagram of an electronic device according to the embodiments of the present disclosure. As shown in FIG. 4, the electronic device includes: a memory 41 and a processor 42; wherein, the memory 41 is used to store programs;

the processor 42 is coupled to the memory and configured to execute the program stored in the memory for:

obtaining a diffusion tensor image to be processed, wherein the diffusion tensor image comprises a diffusion weighted image;

generating a diffusion index image based on the diffusion weighted image;

determining a white matter microstructural feature corresponding to the diffusion tensor image, and determining a hearing state corresponding to the diffusion tensor image according to a mapping relationship between the white matter microstructural feature and the hearing state.

The above-mentioned memory 41 may be configured to store various other data to support operations on the computing device. Examples of such data include instructions for any application or method operating on a computing device. Memory 41 may be implemented by any type of volatile or non-volatile storage apparatus or a combination thereof, such as static random access memory (SRAM), electrically erasable programmable read-only memory (EEPROM), erasable programmable read-only memory (EEPROM), Programmable read-only memory (EPROM), programmable read-only memory (PROM), read-only memory (ROM), magnetic memory, flash memory, magnetic or optical disk.

When the above-mentioned processor 42 executes the program in the memory 41, in addition to the above functions, it can also implement other functions. For details, please refer to the descriptions of the previous embodiments.

Further, as shown in FIG. 4, the electronic device also includes: a display 53, a power supply component 54, a communication component 55 and other components. Only some components are schematically shown in FIG. 4, which does not mean that the electronic device only includes the components shown in FIG. 4.

Correspondingly, embodiments of the present disclosure also provide a readable storage medium storing a computer program. When the computer program is executed by a computer, the steps or functions of the hearing state prediction method provided by the above embodiments can be implemented.

Figure 5:
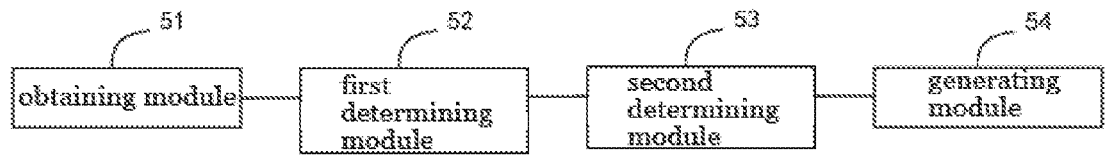
FIG. 5 is a schematic flow chart of a hearing state prediction model training apparatus according to the embodiments of the present disclosure.

FIG. 5 is a schematic flowchart of a hearing state prediction model training apparatus according to the embodiments of the present disclosure. As shown in FIG. 5, the apparatus includes:

obtaining module 501, configured to obtain a diffusion tensor image sample and a preset hearing state corresponding to the diffusion tensor image sample, where the diffusion tensor image sample includes a diffusion weighted image;

first determining module 502, configured to generate a diffusion index image according to the diffusion weighted image; and second determining module 503, configured to determine the white matter microstructural feature corresponding to the diffusion tensor image sample according to the diffusion index image, and determine the hearing state corresponding to the diffusion tensor image sample according to the mapping relationship between the white matter microstructural feature and the hearing state; and generating module 504, configured to determine a consistency between the hearing state and the preset hearing state corresponding to the diffusion tensor image sample, when the consistency between the hearing state and the preset hearing state is greater than or equal to a preset threshold, generating a hearing state prediction model.

In practical applications, the obtained diffusion tensor image may have obvious artifacts due to metal, obvious motion artifacts, etc. during the scanning process. Then, in this embodiment, before obtaining the diffusion tensor image sample, the method may also include an image sample screening process. Specifically, two imaging experts with associate senior titles or above with more than 5 years of experience in radiology examined all DTI image samples one by one and removed DTI images with obvious artifacts.

It is worth noting that the implementation principle of the hearing state prediction model trained by the above method is similar to the implementation principle of the hearing state prediction apparatus provided in FIG. 1. The similarities are as mentioned above and will not be elaborated here.

Figure 6:
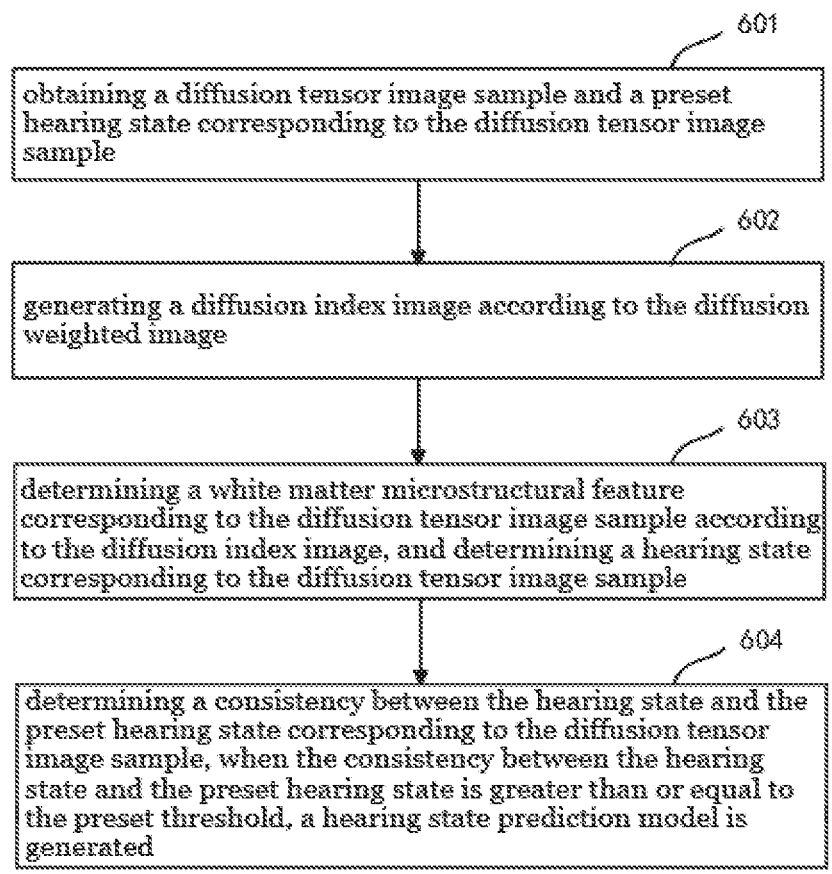
FIG. 6 is a schematic flow chart of a hearing state prediction model training method according to the embodiments of the present disclosure.

FIG. 6 is a schematic flowchart of a hearing state prediction model training method according to the embodiments of the present disclosure. As shown in FIG. 6, the method includes:

601. obtaining a diffusion tensor image sample and a preset hearing state corresponding to the diffusion tensor image sample, wherein the diffusion tensor image sample comprises a diffusion weighted image;

602. generating a diffusion index image according to the diffusion weighted image;

603. determining a white matter microstructural feature corresponding to the diffusion tensor image sample according to the diffusion index image, and determining a hearing state corresponding to the diffusion tensor image sample according to a mapping relationship between the white matter microstructural feature and the hearing state; and

604. determining a consistency between the hearing state and the preset hearing state corresponding to the diffusion tensor image sample, when the consistency between the hearing state and the preset hearing state is greater than or equal to the preset threshold, a hearing state prediction model is generated.

It is worth noting that the implementation principle of the hearing state prediction model trained by the above method is similar to the implementation principle of the hearing state prediction apparatus provided in FIG. 1. The similarities are as mentioned above and will not be elaborated here.

Figure 7:
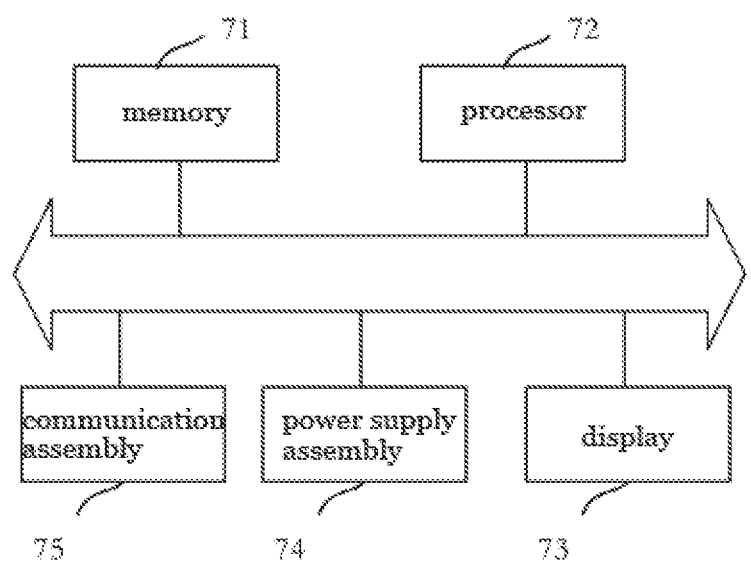
FIG. 7 is a schematic structural diagram of another electronic device according to the embodiments of the present disclosure.

FIG. 7 is a schematic structural diagram of another electronic device according to the embodiments of the present disclosure. As shown in FIG. 7, the electronic device includes: a memory 71 and a processor 72; where, the memory 71 is used to store programs;

the processor 72 is coupled to the memory and configured to execute the program stored in the memory for:

obtaining a diffusion tensor image sample and a preset hearing state corresponding to the diffusion tensor image sample, where the diffusion tensor image sample comprises a diffusion weighted image;

generating a diffusion index image according to the diffusion weighted image;

determining a white matter microstructural feature corresponding to the diffusion tensor image sample according to the diffusion index image, and determining a hearing state corresponding to the diffusion tensor image sample according to a mapping relationship between the white matter microstructural feature and the hearing state;

determining a consistency between the hearing state and the preset hearing state corresponding to the diffusion tensor image sample, when the consistency between the hearing state and the preset hearing state is greater than or equal to the preset threshold, a hearing state prediction model is generated.

The memory 71 described above may be configured to store various other data to support operations on the computing device. Examples of such data include instructions for any application or method operating on a computing device. Memory 71 may be implemented by any type of volatile or non-volatile storage apparatus, or a combination thereof, such as static random access memory (SRAM), electrically erasable programmable read-only memory (EEPROM), erasable programmable read-only memory (EEPROM), Programmable read-only memory (EPROM), programmable read-only memory (PROM), read-only memory (ROM), magnetic memory, flash memory, magnetic or optical disk.

When the above-mentioned processor 72 executes the program in the memory 71, in addition to the above functions, it can also implement other functions. For details, please refer to the descriptions of the previous embodiments.

Further, as shown in FIG. 7, the electronic device also includes: a display 73, a power supply component 74, a communication component 75 and other components.

Only some components are schematically shown in FIG. 7, which does not mean that the electronic device only includes the components shown in FIG. 7.

Correspondingly, embodiments of the present disclosure also provide a readable storage medium storing a computer program. When the computer program is executed by a computer, the steps or functions of the hearing state prediction model training method provided by the above embodiments can be implemented.

The apparatus embodiments described above are merely illustrative, where the units described as separate components may or may not be physically separated, and the components displayed as units may or may not be physical units, i.e., may be located at a place, or may be distributed to multiple network units. Some or all of the modules may be selected according to actual needs to achieve the purpose of the scheme of this embodiment. Those of ordinary skill in the art can understand and implement without creative work.

Through the description of the above implementation modes, those skilled in the art can clearly understand that various implementation modes may be implemented by means of software and a necessary general hardware platform, and of course, by hardware. Based on such understanding, the essence of the foregoing technical solutions or portions making contribution to the prior art may be embodied in the form of software products. The computer software products may be stored in a computer-readable storage medium such as a ROM/RAM, a magnetic disk and an optical disc, including instructions for causing a computer device (which may be a personal computer, a server, or a network device, etc.) to perform the methods described in various embodiments or portions of the embodiments.

Finally, it should be noted that the above embodiments are only used to illustrate the technical solutions of the present disclosure, and are not limited thereto. Although the present disclosure has been described in detail with reference to the foregoing embodiments, those of ordinary skill in the art will understand that the technical solutions described in the foregoing embodiments can be still modified, or some technical features are equivalently replaced. These modifications or replacements do not make the essence of the corresponding technical solutions depart from the spirit and scope of the technical solutions in various embodiments of the present disclosure.

What is claimed is:

1. A hearing state prediction apparatus based on a diffusion tensor image, comprising:
    an obtaining module, configured to obtain a diffusion tensor image to be processed, wherein the diffusion tensor image comprises a diffusion-weighted image;
    a first determining module, configured to generate a diffusion index image according to the diffusion-weighted image; and
    a second determining module, configured to perform feature extraction on the diffusion index image to obtain a first depth feature; perform segmentation on the diffusion index image to obtain multiple segmented regions; perform feature extraction on the multiple segmented regions to obtain a second depth feature; and input the first depth feature and the second depth feature to a first deep learning model to obtain a hearing state corresponding to the depth feature, and the first deep learning model is trained to determine the hearing state.

2. The apparatus according to claim 1, wherein when the first determining module generates a diffusion index image according to the diffusion-weighted image, it is specifically configured to:
    determine a diffusion tensor according to the diffusion-weighted image;
    determine a diffusion eigenvalue according to the diffusion tensor;
    determine the diffusion index data according to the diffusion eigenvalue; and
    generate the diffusion index image according to the diffusion index data.

3. The apparatus according to claim 1, wherein when the second determining module determines the white matter microstructural feature corresponding to the diffusion tensor image according to the diffusion index image, it is specifically configured to:
    perform filtering processing on the diffusion index image to obtain a processed diffusion index image;
    perform feature extraction on the processed diffusion index image to obtain a third depth feature;
    perform segmentation on the processed diffusion index image to obtain multiple segmented regions;
    perform feature extraction on the multiple segmented regions to obtain a fourth depth feature; and
    determine the white matter microstructure feature corresponding to the diffusion tensor image according to the third depth feature and the fourth depth feature.

4. The apparatus according to claim 3, wherein the second determining module performs feature extraction on the processed diffusion index image to obtain a third depth feature, is specifically configured to:
    perform analyzing on the processed diffusion index image using a first machine learning model to obtain a depth feature generation graph corresponding to the processed diffusion index image, and the first machine learning model is trained to determine the depth feature generation graph;
    perform downsampling on the depth feature generation graph to obtain a depth feature graph;
    extract a gray level co-occurrence matrix based on the depth feature graph; and
    the gray level co-occurrence matrix is determined as the third depth feature.

5. The apparatus according to claim 4, wherein the first machine learning model comprises an adversarial diffusion model including mixed noise.

6. The apparatus according to claim 5, wherein the second determining module performing feature extraction on the multiple segmented regions to obtain fourth depth feature, is specifically configured to:
    perform analyzing on the multiple segmented regions using a second machine learning model to obtain fourth depth feature information corresponding to each of the multiple segmented regions, the second machine learning model is trained to obtain the fourth depth feature information corresponding to the segmented regions.

7. The apparatus according to claim 3, the second determining module determining the corresponding diffusion tensor image according to the mapping relationship between the white matter microstructural feature and the hearing state, is specifically configured to:
    determine the hearing state to which the white matter microstructure belongs according to the white matter microstructural feature and a white matter microstructural feature threshold corresponding to each hearing state.

8. The apparatus according to claim 1, wherein the diffusion index image comprises one or a combination of the following: an anisotropic fraction graph, an average diffusion coefficient graph, an axial diffusion coefficient graph, and a radial diffusion coefficient graph.

9. A hearing state prediction method based on a diffusion tensor image, comprising:
    obtaining a diffusion tensor image to be processed, wherein the diffusion tensor image comprises a diffusion-weighted image;
    generating a diffusion index image based on the diffusion-weighted image;
    performing feature extraction on the diffusion index image to obtain a first depth feature;
    performing segmentation on the diffusion index image to obtain multiple segmented regions;
    performing feature extraction on the multiple segmented regions to obtain a second depth feature; and
    inputting the first depth feature and the second depth feature to a first deep learning model to obtain a hearing state corresponding to the depth feature, and the first deep learning model is trained to determine the hearing state.

10. A hearing state prediction model training apparatus, comprising:
an obtaining module, configured to obtain a diffusion tensor image sample and a preset hearing state corresponding to the diffusion tensor image sample, wherein the diffusion tensor image sample comprises a diffusion-weighted image;
a first determining module, configured to generate a diffusion index image according to the diffusion-weighted image;
a second determining module, configured to perform feature extraction on the diffusion index image to obtain a first depth feature; perform segmentation on the diffusion index image to obtain multiple segmented regions; perform feature extraction on the multiple segmented regions to obtain a second depth feature; and input the first depth feature and the second depth feature to a first deep learning model to obtain a hearing state corresponding to the depth feature, and the first deep learning model is trained to determine the hearing state; and
generating module, configured to determine a consistency between the hearing state and the preset hearing state corresponding to the diffusion tensor image sample, when the consistency between the hearing state and the preset hearing state is greater than or equal to a preset threshold, generating a hearing state prediction model.

11. A training method for a hearing state prediction model, comprising:
obtaining a diffusion tensor image sample and a preset hearing state corresponding to the diffusion tensor image sample, wherein the diffusion tensor image sample comprises a diffusion-weighted image;
generating a diffusion index image according to the diffusion-weighted image;
performing feature extraction on the diffusion index image to obtain a first depth feature;
performing segmentation on the diffusion index image to obtain multiple segmented regions;
performing feature extraction on the multiple segmented regions to obtain a second depth feature; and inputting the first depth feature and the second depth feature to a first deep learning model to obtain a hearing state corresponding to the depth feature, and the first deep learning model is trained to determine the hearing state; and
determining a consistency between the hearing state and the preset hearing state corresponding to the diffusion tensor image sample, when the consistency between the hearing state and the preset hearing state is greater than or equal to the preset threshold, a hearing state prediction model is generated.

* * * * *